United States Patent [19]

Walker

[11] 4,150,153
[45] Apr. 17, 1979

[54] 1-(NAPHTHYLETHYL)IMIDAZOLE DERIVATIVES

[75] Inventor: Keith A. M. Walker, Palo Alto, Calif.

[73] Assignee: Syntex (U.S.A.) Inc., Palo Alto, Calif.

[21] Appl. No.: 848,548

[22] Filed: Nov. 4, 1977

Related U.S. Application Data

[60] Continuation-in-part of Ser. No. 796,624, May 13, 1977, abandoned, which is a division of Ser. No. 666,388, Mar. 17, 1976, abandoned.

[51] Int. Cl.² .................. A61K 31/415; C07D 233/64
[52] U.S. Cl. ............................ 424/273 R; 548/336; 548/341
[58] Field of Search .................. 548/341, 336; 424/273 R

[56] References Cited

U.S. PATENT DOCUMENTS

| 3,575,999 | 4/1971 | Godefroi et al. ............... 548/336 |
| 3,658,813 | 4/1972 | Godefroi et al. ............... 548/341 |

OTHER PUBLICATIONS

Krasovskii et al., Chem. Abst., 1970, vol. 73, No. 109740z.
Thizy et al., Chem. Abst., 1976, vol. 84, No. 13501y.
Godefroi et al., III, 1969, vol. 12, pp. 784–791.

*Primary Examiner*—Richard Raymond
*Attorney, Agent, or Firm*—Alan M. Krubiner; Gerard A. Blaufarb

[57] ABSTRACT

Compounds of the formula

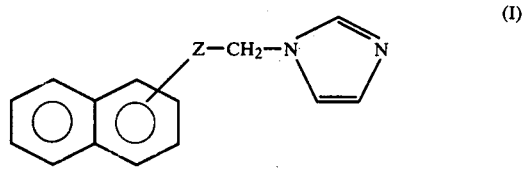

(I)

wherein Z is hydroxymethylene, esterified hydroxymethylene, carbonyl, or ketal-, thioketal- or hemithioketal- protected carbonyl, and the pharmaceutically acceptable acid addition salts thereof, are useful as anticonvulsant and anti-secretory agents.

15 Claims, No Drawings

1-(NAPHTHYLETHYL)IMIDAZOLE DERIVATIVES

RELATED APPLICATIONS

This is a continuation-in-part of co-pending application Ser. No. 796,624, filed May 13, 1977, now abandoned, which in turn is a division of application Ser. No. 666,388, filed Mar. 17, 1976, now abandoned.

DESCRIPTION OF THE INVENTION

The present invention relates to certain 1-(naphthylethyl)imidazole derivatives. More particularly, the present invention relates to compounds of formula (I), namely:

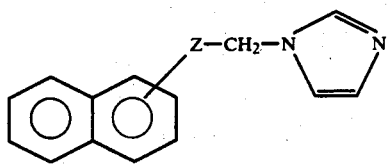

(I)

wherein Z is hydroxymethylene, esterified hydroxymethylene, carbonyl, or ketal-, thioketal- or hemithioketal- protected carbonyl; and the pharmaceutically acceptable acid addition salts thereof.

As used in the specification and appended claims, unless specified to the contrary, the following terms have the meanings indicated. The term "esterified hydroxymethylene" refers to a hydroxymethylene group which has been esterified with an alkanoic acid having from 1 to 8 carbon atoms or with benzoic acid. Typical alkanoic acids which may be mentioned are formic acid, acetic acid, propionic acid, butyric acid, isobutyric acid, valeric acid, isovaleric acid, caproic acid and octanoic acid. The term "ketal-protected carbonyl" refers to (i) a carbonyl group protected as an acyclic ketal derived from a monohydric straight chain alkanol having from 1 to 4 carbon atoms such as, for example, the dimethyl-, diethyl-, di(n-propyl)- and di(n-butyl) ketals, and (ii) a carbonyl group protected as a cyclic ketal derived from a dihydric alcohol having 2 or 3 carbon atoms which may optionally be substituted by one or more methyl groups, for example, the ethylenedioxy-, 1,3-propylenedioxy-, 1,2-propylenedioxy-, 2,2-dimethyl-1,3-propylenedioxy, 1-methyl-1,3-propylenedioxy, 1,3-dimethyl-1,3-propylenedioxy- and 2,3-butylenedioxy-ketals. The term "thioketal- protected carbonyl" shall mean (i) a carbonyl group protected as an acyclic thioketal derived from a straight or branched chain alkylthiol having from 1 to 4 carbon atoms, such as the bis(methylthio)-, bis(ethylthio)-, bis(n-propylthio)-, bis(isopropylthio)-and bis(isobutylthio)- ketals, or from thiophenol or benzylmercaptan (i.e., the bis(phenylthio)- and bis(benzylthio)-ketals), and (ii) a carbonyl group protected as a cyclic thioketal derived from an alkylenedithiol having 2 or 3 carbon atoms which may optionally be substituted by one or more methyl groups, for example, the ethylenedithio-, 1,3-propylenedithio, and 2,2-dimethyl-1,3-propylenedithio-ketals. The term "hemithioketal-protected carbonyl" shall mean a carbonyl group protected as a cyclic hemithioketal derived from 2-mercaptoethanol or 3-mercapto-1-propanol. The term "pharmaceutically acceptable acid addition salts" refers to salts of the free bases of formula (I), which salts possess the desired pharmacological activity and which are neither biologically nor otherwise undesirable. Such salts may be formed with inorganic acids such as hydrochloric acid, hydrobromic acid, sulfuric acid, nitric acid or phosphoric acid; or with organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

Compounds of formula (I) wherein Z is hydroxymethylene or esterified hydroxymethylene or hemithioketal protected carbonyl possess a chiral center. Accordingly, these compounds may be prepared in either optically active form, or as a racemic mixture. Unless otherwise specified, the compounds described herein are all in the racemic form. However, the scope of the subject invention is not to be limited to the racemic form but is to encompass the individual optical isomers of the subject compounds.

If desired, compounds of formula (I) wherein Z is hydroxymethylene or esterified hydroxymethylene or hemithicketal protected carbonyl may be prepared in optically active form by conventional resolution means known per se, for example, by the separation (e.g., fractional crystallization) of the diastereomeric salts formed by reaction of, e.g., racemic compounds of formula (I) wherein Z is hydroxymethylene or esterified hydroxymethylene, or hemithioketal protected carbonyl with an optically active acid, or by separation of the diastereomeric esters formed by reaction of such a racemic alcohol wherein Z is hydroxymethylene with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, and the like. The separated pure diasteromeric salts or esters may then be cleaved by standard means to afford the respective optical isomers of the desired compound.

Compounds of formula (I) exhibit a broad spectrum of CNS related activity such as anticonvulsant activity (as demonstrated by the maximal electroshock seizure test), anorexigenic, antidepressant and muscle relaxing activity; as well as activity of other types such as inhibition of gastric secretion and antihypertensive activities.

One aspect of the present invention relates to a method for treating and/or preventing convulsions in a mammalian subject comprising administering a therapeutically effective amount of a compound of formula (I), or a pharmaceutically acceptable acid addition salt thereof. Another aspect of the present invention relates to pharmaceutical compositions useful for the treatment and/or prevention of convulsions in a mammalian subject comprising a compound of formula (I), or a pharmaceutically acceptable acid addition salt thereof, in admixture with a pharmaceutically acceptable non-toxic carrier. For this utility compounds of formula (I) wherein Z is carbonyl or ketal-protected carbonyl are particularly preferred.

Yet another aspect of the present invention relates to a method for inhibiting gastric secretion in a mammalian subject comprising administering a therapeutically effective amount of a compound of formula (I), or a pharmaceutically acceptable acid addition salt thereof. Still another aspect of the present invention relates to pharmaceutical compositions useful for the inhibition of gastric secretion in a mammalian subject comprising a compound of formula (I), or a pharmaceutically acceptable acid addition salt thereof, in admixture with a pharmaceutically acceptable non-toxic carrier. For this utility compounds of formula (I) wherein Z is thioketal-protected carbonyl are particularly preferred.

In the practice of the above described methods of the present invention a therapeutically effective amount of the compound of formula (I) or a pharmaceutical composition containing same is administered via any of the usual and acceptable methods known in the art, either singly or in combination with another compound or compounds of the present invention or other pharmaceutical agents. These compounds or compositions can thus be administered orally or parenterally (i.e. intramuscularly, subcutaneously and intraveneously), and can be administered either in the form of solid or liquid dosages including tablets, solutions, suspensions, and the like, as discussed in more detail hereinbelow. Oral administration is preferred.

The administration can be conducted in a single unit dosage form with continuous therapy or in single dosage therapy ad libitum. The method of the present invention may be practiced when relief of symptoms is specifically required, i.e. therapeutically, or as continuous or prophylactic treatment.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount for anticonvulsant use ranges from about 0.1 to about 300 mg./kg. body weight per day and preferably about from 1 to about 100 mg./kg. body weight per day. In alternate terms, for an average adult human subject, a therapeutically effective amount in accordance herewith would be, in preferred embodiments, from about 70 mg. to about 7 g. per day per subject. A therapeutically effective amount for inhibition of gastric secretion ranges from about 0.1 to about 300 mg./kg. body weight per day and preferably from about 0.25 to about 100 mg./kg. body weight per day. In alternate terms, for an average adult human subject, a therapeutically effective amount in accordance herewith would be, in preferred embodiments from about 18 mg. to about 7 g per day per subject.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject.

Compounds of formula (I) wherein Z is hydroxymethylene or carbonyl have been previously described in applicant's co-pending application Ser. No. 796,624, filed May 13, 1977, as intermediates useful for the preparation of compounds having antifungal, antibacterial and antiprotozoal activity. The disclosure in said co-pending application is hereby incorporated by reference herein.

The compounds of the present invention may be prepared according to methods well known in the art. For example, compounds of formula (I) wherein Z is carbonyl may be prepared in a manner analogous to that described in U.S. Pat. No. 3,717,655 to Godefroi et al. This method comprises reacting a halomethyl naphthyl ketone with imidazole in an inert organic solvent. The starting halomethyl naphthyl ketones are known or may be prepared by halogenation of the corresponding methyl naphthyl ketone by known means, for example, utilizing cupric bromide. The preparation of ketones of formula (I) by the above described method may be carried out in an inert organic solvent, for example, dimethylformamide at a temperature between about $-10°$ and $+40°$ C.

Preparation of compounds of formula (I) wherein Z is hydroxymethylene may be accomplished by the reduction of the corresponding ketone or acid addition salt thereof under standard conditions, for example, by the use of sodium tetrahydroborate in a protic solvent, for example, methanol, at a temperature between about $-20°$ and $+20°$ C.

Compounds of formula (I) wherein Z is esterified hydroxymethylene may be prepared under usual esterification conditions from the corresponding alcohol by treatment of the alcohol with the desired acid halide or anhydride in the presence of a base, preferably a tertiary amine such as pyridine or triethylamine, at a temperature between about 0° and $+40°$ C. in a solvent such as pyridine, tetrahydrofuran, dichloromethane, chloroform, and the like.

Certain compounds of formula (I) wherein Z is ketal-protected carbonyl may be prepared from the corresponding ketone by treatment of the ketone (or an acid addition salt thereof) with the desired dihydric alcohol in the presence of a strong acid, for example a sulfonic acid such as p-toluenesulfonic acid or a Lewis acid such as boron trifluoride. Water is preferably removed as an azeotrope with the solvent, for example an aromatic hydrocarbon such as benzene or toluene, at a temperature sufficient to effect such azeotropic removal, e.g. from about 75° to about 150° C.

Compounds of formula (I) wherein Z is thioketal-protected carbonyl may be prepared from the corresponding ketones by treatment of the ketone (or an acid addition salt thereof) with the desired thiol or dithiol, optionally in the presence of a mineral acid such as hydrochloric acid, an organic sulfonic acid such as methanesulfonic acid or a Lewis acid such as boron trifluoride or zinc chloride at a temperature between about 0° and $+100°$ C., preferably between about 0° and 25° C.

Compounds of formula (I) wherein Z is hemithioketal-protected carbonyl may be prepared from the corresponding ketones by treatment of the ketone with the desired mercaptoalkanol under conditions similar to those described above for ketal formation.

Compounds of formula (I) wherein Z is ketal-protected carbonyl may also be prepared according to the following reaction sequence:

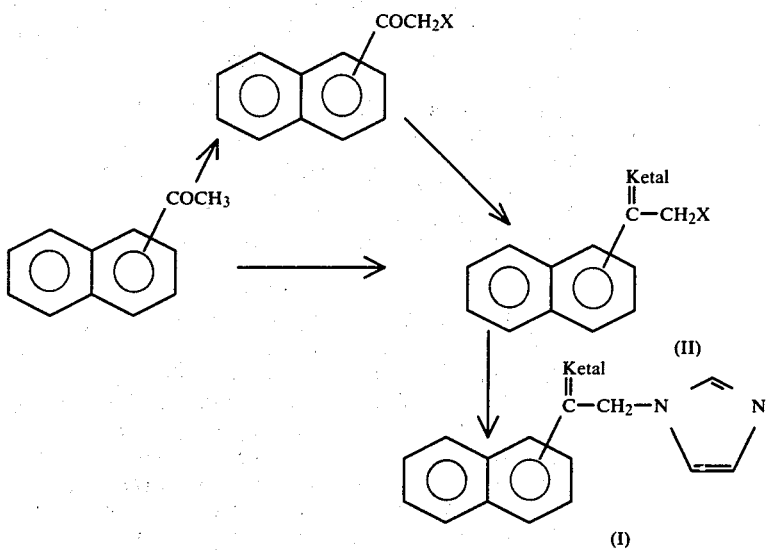

wherein X is halo (especially chloro or bromo), as described in U.S. Pat. Nos. 3,793,453 and 3,575,999 in the corresponding phenyl series. In this sequence the naphthyl methyl ketone is either first halogenated to the naphthyl halomethyl ketone, followed by ketalization or both steps are performed concurrently. Ketalization to form cyclic ketals may be performed essentially as described above. Ketalization to form acyclic ketals may be performed by employing an orthoester (e.g. methyl orthoformate or ethyl orthoformate) in the presence of an acid or Lewis acid, e.g. boron trifluoride, p-toluenesulfonic acid, perchloric acid, fuming sulfuric acid, and the like. The haloketal (II) is then converted to (I) by treatment with an alkali metal salt, e.g. the sodium salt, of imidazole in a polar aprotic solvent such as dimethylformamide, dimethylsulfoxide or tetrahydrofuran at a temperature between about 20° and 130° C.

Compounds of formula (I) wherein Z is hydroxymethylene may also be prepared according to the following reaction sequence:

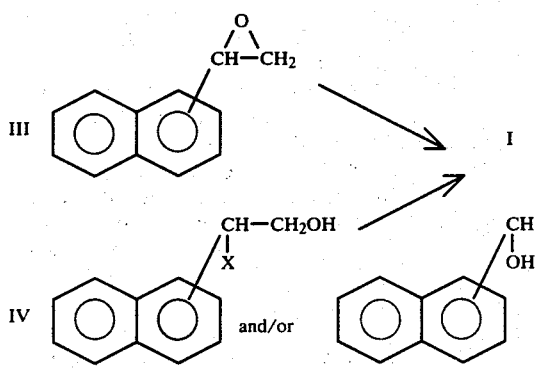

wherein the epoxide (III) or the halohydrin (IV) is treated with imidazole and/or an alkali metal salt (preferably the sodium salt) thereof in a polar aprotic solvent such as dimethylformamide, dimethylsulfoxide or tetrahydrofuran at a temperature between about 0° and 100° C. Treatment of the epoxide requires one mole of imidazole in the presence of 0.05-1 mole of imidazole salt.

Treatment of the halohydrin requires slightly over one mole of imidazole salt, since the halohydrin is first converted in situ to the epoxide.

The subject compounds of formula (I) can be isolated as free bases; however, since many of the compounds in base form are oils and gums and/or not water soluble it is often more convenient to isolate and further characterize such compounds as acid addition salts. These salts are prepared in the usual manner, i.e., by reaction of the free base with a suitable inorganic or organic acid, for example one of the pharmaceutically acceptable acids described above. If desired, the salt can be readily converted to the free base by treatment with a base such as potassium or sodium carbonate or potassium or sodium hydroxide.

In summary, another aspect of the present invention concerns a process for the preparation of a free base compound of the formula

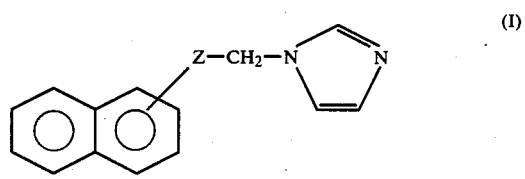

wherein Z is hydroxymethylene, esterified hydroxymethylene, carbonyl, or ketal-, hemithioketal- or thioketal-protected carbonyl; or a pharmaceutically acceptable non-toxic acid addition salt thereof, which process comprises:

(a) the preparation of a compound of formula (I) wherein Z is carbonyl by reaction of a halomethyl naphthyl ketone with imidazole, or (b) the preparation of a compound of formula (I) wherein Z is hydroxymethylene by reduction of a compound of formula (I) wherein Z is carbonyl, or (c) the preparation of a compound of formula (I) wherein Z is esterified hydroxymethylene by esterification of a compound of formula (I) wherein Z is hydroxymethylene, or (d) the preparation of a compound of formula (I) wherein Z is ketal protected carbonyl by ketalization of a compound of formula (I) wherein Z is carbonyl, or (e) the preparation of a compound of formula (I) wherein Z is hemithioketal-protected carbonyl by hemithioketalization of a compound of formula (I) wherein Z is carbonyl, or (f) the preparation of a compound of formula (I) wherein Z is thioketal-protected carbonyl by thioketalization of a compound of formula (I) wherein Z is carbonyl, or (g) the preparation of a compound of formula (I) wherein Z is ketal-protected carbonyl by reaction of a compound of the formula

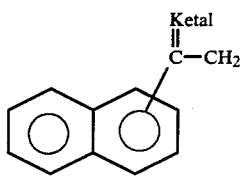

wherein X is halo, with an alkali metal salt of imidazole, or (h) the preparation of a compound of formula (I) wherein Z is hydroxymethylene by reaction of a compound of the formula

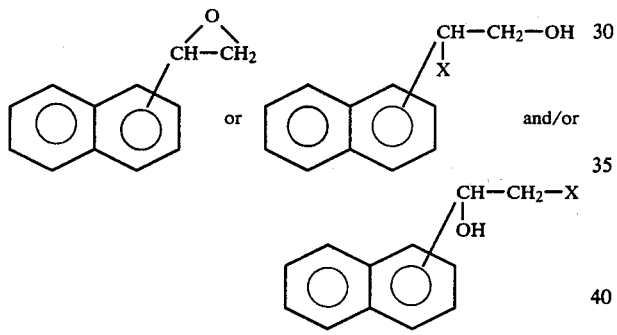

with imidazole and/or an alkali metal salt thereof, and (i) optionally converting a free base to the corresponding acid addition salt, or (j) optionally converting an acid addition salt to the corresponding free base.

The following specific description is given to enable those skilled in the art to more clearly understand and practice the present invention. It should not be considered as a limitation upon the scope of the invention but merely as illustrative and representative thereof.

EXAMPLE 1

To a stirred, ice-cooled slurry of 35 g. of imidazole in 25 ml. of dimethylformamide is added 24.9 g. of bromomethyl 2-naphthyl ketone. The mixture is stirred for 2 hours at 0° C., and then allowed to come to room temperature and stirred overnight. The solution is poured into water and the resulting sticky solid filtered off, washed with water and dissolved in benzene. Thereafter the resultant benzene solution is dried (azeotroped) to afford 1-(2-naphthoylmethyl)imidazole which is converted to its hydrochloride acid addition salt by addition of ethereal hydrogen chloride until precipitation is complete. The salt is crystallized by the addition of ethyl acetate and the resulting solid recrystallized from methanol/acetone to yield colorless needles of 1-(2-naphthoylmethyl)imidazole hydrochloride, m.p. 226°–228.5° C. (decomp.).

EXAMPLE 2

To 9.4 g. of the above obtained 1-(2-naphthoylmethyl)imidazole hydrochloride in 200 ml. of methanol at 0°–5° C. is added, with stirring, excess sodium tetrahydroborate. After stirring for 30 minutes at 0° C., the reaction mixture is evaporated to dryness. The resultant residue is treated with 200 ml. of water and the product which crystallizes is filtered off, washed with water and recrystallized from ethyl acetate to yield 1-[2-hydroxy-2-(2-naphthyl)ethyl]imidazole as off-white blades, m.p. 156°–160.5° C. (slight decomp.).

EXAMPLE 3

Methyl 1-naphthyl ketone (10.1 g.), in 50 ml of a 1:1 mixture of chloroform and ethyl acetate is treated with 26.5 g. of copper (II) bromide. The resulting reaction mixture is heated under reflux with vigorous stirring until the evolution of hydrogen bromide ceases. When the reaction is complete the solvent is removed, ether is added and the copper (I) bromide is removed by filtration. Evaporation of the filtrate under reduced pressure yields crude bromomethyl 1-naphthyl ketone.

The above obtained bromomethyl 1-naphthyl ketone is then treated according to the procedure previously recited in Example 1 to afford 1-(1-naphthoylmethyl)imidazole which after 2 recrystallizations from benzene gave colorless flakes, m.p. 113.5°–117° C.

EXAMPLE 4

To 7.0 g. of the above 1-(1-naphthoylmethyl)imidazole in 50 ml. methanol at 0°–5° C. is added with stirring excess sodium tetrahydroborate. After stirring for thirty minutes the solvent was removed and the residue treated with water. The product was filtered off, washed with water and recrystallized from ethyl acetate as snow-white microcrystals of 1-[2-hydroxy-2-(1-naphthyl)ethyl]imidazole (5.60 g.) m.p. 112.5°–115° C. (slight decomp.).

EXAMPLE 5

A mixture of 5.45 g. of 1-(2-naphthoylmethyl)imidazole hydrochloride, 2.49 g. ethylene glycol and 7.6 g. p-toluenesulfonic acid monohydrate in 50 ml. of toluene is heated overnight under reflux through a Dean-Stark trap. The trap is then replaced by a separatory funnel containing 4 A molecular seives and heating is continued for a further day. After cooling, the mixture is treated with 200 ml. of ethyl acetate, neutralized by pouring into excess aqueous potassium carbonate and the organic phase separated and dried (MgSO₄) to afford a solution of 1-[2,2-ethylenedioxy-2-(2-naphthyl)ethyl]imidazole. The hydrochloride salt is prepared by dropwise addition of ethereal hydrogen chloride until precipitation is complete. Filtration and recrystallization from acetone/methanol gives 3.9 g. pure hydrochloride. m.p. 269°–270° C.

EXAMPLE 6

A solution of 2.72 g. of 1-(2-naphthoylmethyl)imidazole hydrochloride in 6 ml. of 98% methanesulfonic acid is treated at room temperature with 4 ml. of n-propyl mercaptan and the mixture stirred overnight under nitrogen. The resulting solution is added to excess aqueous potassium carbonate, the product extracted with ether and the extracts washed and dried (MgSO₄)

to afford a solution of 1-[2,2-bis(n-propylthio)-2-(2-naphthyl)ethyl]imidazole. Dropwise addition of ethereal hydrogen chloride precipitates 2.80 g. of the hydrochloride which is recrystallized from acetone/methanol to give 2.55 g. pure product, m.p. 188°-189.5° C.

EXAMPLE 7

A solution of 1.19 g. 1-[2-hydroxy-2-(2-naphthyl)ethyl]imidazole in 20 ml. of pyridine is treated dropwise with stirring with 0.72 ml. of benzoyl chloride and the mixture stirred overnight. The resulting solution is poured into 100 ml. water, extracted with ethyl acetate and the extracts washed, dried (MgSO4) and evaporated in vacuo to remove residual pyridine and afford 1-[2-benzoyloxy-2(2-naphthyl)ethyl]imidazole. The residue is dissolved in ether, treated with ethereal hydrogen chloride and the resulting precipitate recrystallized from acetone/methanol to give 1.3 g. of hydrochloride salt, m.p. 219°-219.5° C.

EXAMPLE 8

Repeating the procedure of Example 5, utilizing 1-(2-naphthoylmethyl)imidazole, 1-(1-naphthoylmethyl)imidazole, or an acid addition salt thereof, and the appropriate alkylenediol, there may be prepared the following compounds which may be further characterized as the acid addition salts indicated:
1-[2,2-(1,3-propylenedioxy)-2-(2-naphthyl)ethyl]imidazole-hydrochloride salt, m.p. 258°-260° C.
1-[2,2-(2,2-dimethyl-1,3-propylenedioxy)-2-(2-naphthyl)ethyl]imidazole-hydrochloride salt, m.p. 284°-288° C.
1-[2,2-(1-methyl-1,3-propylenedioxy)-2-(2-naphthyl)ethyl]imidazole-hydrochloride salt, m.p. 171.5°-172.5° C.
1-[2,2-ethylenedioxy-2-(1-naphthyl)ethyl]imidazole-hydrochloride salt, m.p. 256.5°-257° C.
1-[2,2-(1,3-propylenedioxy)-2-(1-naphthyl)ethyl]imidazole
1-[2,2-(2,2-dimethyl-1,3-propylenedioxy)-2-(1-naphthyl)ethyl]imidazole
1-[2,2-(1-methyl-1,3-propylenedioxy)-2-(1-naphthyl)ethyl]imidazole
1-[2,2-(1,2-propylenedioxy)-2-(2-naphthyl)ethyl]imidazole
1-[2,2-(1,2-propylenedioxy)-2-(1-naphthyl)ethyl]imidazole
1-[2,2-(2,3-butylenedioxy)-2-(2-naphthyl)ethyl]imidazole
1-[2,2-(2,3-butylenedioxy)-2-(1-naphthyl)ethyl]imidazole.

EXAMPLE 9

Repeating the procedure of Example 6, utilizing 1-(2-naphthoylmethyl)imidazole, 1-(1-naphthoylmethyl)imidazole, or an acid addition salt thereof, and the appropriate alkylthiol or alkylenedithiol, there may be prepared the following compounds which may be further characterized as the acid addition salts indicated:
1-[2,2-bis(methylthio)-2-(2-naphthyl)ethyl]imidazole-hydrochloride salt, m.p. 206.5°-207.5° C. (foaming)
1-[2,2-bis(ethylthio)-2-(2-naphthyl)ethyl]imidazole-hydrochloride salt, m.p. 205°-208.5° C.
1-[2,2-bis(isopropylthio)-2-(2-naphthyl)ethyl]imidazole-hydrochloride salt, m.p. 232.5°-235° C.
1-[2,2-bis(isobutylthio)-2-(2-naphthyl)ethyl]imidazole-hydrochloride salt, m.p. 260°-262° C. (decomp.)
1-[2,2-ethylenedithio-2-(2-naphthyl)ethyl]imidazole-hydrochloride salt, m.p. 247.5°-248.5° C. (decomp.)
1-[2,2-(1,3-propylenedithio)-2-(2-naphthyl)ethyl]imidazole-hydrochloride salt, m.p. 262.5°-264.5° C. (decomp.)
1-[2,2-bis(methylthio)-2-(1-naphthyl)ethyl]imidazole
1-[2,2-bis(isopropylthio)-2-(1-naphthyl)ethyl]imidazole
1-[2,2-ethylenedithio-2-(1-naphthyl)ethyl]imidazole
1-[2,2-bis(ethylthio)-2-(1-naphthyl)ethyl]imidazole
1-[2,2-bis(n-propylthio)-2-(1-naphthyl)ethyl]imidazole
1-[2,2-bis(n-butylthio)-2-(1-naphthyl)ethyl]imidazole
1-[2,2-bis(phenylthio)-2-(2-naphthyl)ethyl]imidazole-hydrochloride salt, m.p. 180°-182.5° C. (decomp.)
1-[2,2-bis(benzylthio)-2-(2-naphthyl)ethyl]imidazole-hydrochloride salt, m.p. 181°-182° C. (foaming)
1-[2,2-bis(n-butylthio)-2-(2-naphthyl)ethyl]imidazole
1-[2,2-(1,3-propylenedithio)-2-(1-naphthyl)ethyl]imidazole
1-[2,2-bis(benzylthio)-2-(1-naphthyl)ethyl]imidazole
1-[2,2-bis(phenylthio)-2-(1-naphthyl)ethyl]imidazole

EXAMPLE 10

Repeating the procedure of Example 7, utilizing 1-[2-hydroxy-2-(2-naphthyl)ethyl]imidazole or 1-[2-hydroxy-2-(1-naphthyl)ethyl]imidazole, and the appropriate acid halide or anhydride, there may be prepared the following compounds:
1-[2-acetoxy-2-(2-naphthyl)ethyl]imidazole,
1-[2-propionyloxy-2-(2-naphthyl)ethyl]imidazole,
1-[2-butyryloxy-2-(2-naphthyl)ethyl]imidazole,
1-[2-isobutyryloxy-2-(2-naphthyl)ethyl]imidazole,
1-[2-hexanoyloxy-2-(2-naphthyl)ethyl]imidazole,
1-[2-acetoxy-2-(1-naphthyl)ethyl]imidazole,
1-[2-propionyloxy-2-(1-naphthyl)ethyl]imidazole,
1-[2-butyryloxy-2-(1-naphthyl)ethyl]imidazole,
1-[2-isobutyryloxy-2-(1-naphthyl)ethyl]imidazole,
1-[2-hexanoyloxy-2-(1-naphthyl)ethyl]imidazole.
1-[2-benzoyloxy-2-(1-naphthyl)ethyl]imidazole.

EXAMPLE 11

A solution of 2.49 g. of bromomethyl 2-naphthyl ketone, 1.7 g. trimethyl orthoformate and a few crystals of p-toluenesulfonic acid (anhydrous) in 20 ml. anhydrous methanol is heated under reflux for two hours. After cooling to room temperature, two drops of phenolphthalein solution are added and a solution of sodium methoxide in methanol is added dropwise until a pink color persists. After removal of the solvent under reduced pressure the resulting oil is dissolved in ether, decolorized with charcoal and the ether removed to give 2.95 g (100%) of bromomethyl 2-naphthyl ketone dimethyl ketal as a colorless oil.

Sodium hydroxide (0.40 g. of 50% dispersion in mineral oil) is added to 0.61 g. imidazole in 10 ml dimethylformamide and the mixture stirred at room temperature until the evolution of hydrogen is complete. Bromomethyl 2-naphthoyl ketone dimethyl ketal (2.21 g.) in 5 ml. dimethylformamide is then added and the mixture stirred for 24 hours at 110° under nitrogen. The resulting solution is poured into water (400 ml), extracted with ether (400 ml total), and the extracts washed, dried (MgSO4) and evaporated. The resulting crude solid (2.2 g) is recrystallized from toluene to give 1-[2-(2-naphthyl)-2,2-dimethoxyethyl]imidazole as a colorless solid.

EXAMPLE 12

Repeating the procedure of Example 11, utilizing bromomethyl 2-naphthyl ketone or bromomethyl 1- naphthyl ketone and the appropriate alkyl orthoformate, there may be prepared the following compounds:
1-[2-(2-naphthyl)-2,2-diethoxyethyl]imidazole
1-[2-(2-naphthyl)-2,2-di(n-propoxy)ethyl]imidazole
1-[2-(2-naphthyl)-2,2-di-(n-butoxy)ethyl]imidazole
1-[2-(1-naphthyl)-2,2-dimethoxyethyl]imidazole
1-[2-(1-naphthyl)-2,2-diethoxyethyl]imidazole
1-[2-(1-naphthyl)-2,2-di(n-propoxy)ethyl]imidazole
1-[2-(1-naphthyl)-2,2-di(n-butoxy)ethyl]imidazole.

EXAMPLE 13

1-[2-Naphthoylmethyl]imidazole hydrochloride (540 mg) and p-toluenesulfonic acid monohydrate (570 mg) in toluene (10 ml) containing a little benzene are treated with 2-mercaptoethanol (4 ml). A pressure-equalized addition funnel filled with activated 4 A molecular sieves in toluene is placed above the flask as a modified Dean-Stark trap and the mixture heated under reflux with stirring for 18 hours. The resulting mixture is then added with stirring to excess aqueous potassium carbonate, the product extracted with ether (with filtration) and the extracts washed, dried (MgSO₄) and evaporated. Purification by chromatography on silica gel eluting with ethyl acetate gives pure 1-[2-naphthoylmethyl]imidazole ethylene hemithioketal.

Similarly using the appropriate ketone or an acid addition salt thereof and a correspondingly suitable amount of p-toluene sulfonic acid in benzene and/or toluene with 2-mercaptoethanol or 3-mercaptopropanol there may be obtained:
1-[2-naphthoylmethyl]imidazole 1,3-propylenehemithioketal
1-[1-naphthoylmethyl]imidazole ethylene hemithioketal
1-[1-naphthoylmethyl]imidazole 1,3-propylenehemithioketal.

EXAMPLE 14

Ethereal hydrogen chloride is added dropwise to a solution of 1.0 g. 1-(2-naphthoylmethyl)imidazole in 100 ml. anhydrous benzene until precipitation is complete. The product is filtered, washed with ether, air dried and recrystallized from methanol/acetone to yield 1-(2-naphthoylmethyl)imidazole hydrochloride, m.p. 226°–228.5° C. (decomp.)

In a similar manner, all compounds of formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 15

1-(2-Naphthoylmethyl)imidazole hydrochloride (1.0 g.) suspended in 50 ml. of ether is stirred with excess dilute aqueous potassium carbonate solution until the salt is completely dissolved. The organic layer is then separated, washed twice with water, dried over magnesium sulfate and evaporated to yield 1-(2-naphthoylmethyl)imidazole.

In a similar manner the acid addition salts of all compounds of formula (I) may be converted to the corresponding compounds in free base form.

EXAMPLE 16

Maximal Electroshock Test in Mice

This test was performed in the standard manner, essentially as described by Swinyard et al., J. Pharm. Exp. Ther., Vol. 106, pp. 319–330 (1952).

Groups of 10 male Hilltop ICR-derived mice weighing 20–30 grams were dosed intraperitoneally with a solution or suspension of drug in saline 15 minutes prior to a transcorneal maximal electroshock (50 milliamps, 0.2 seconds). The mice were observed for the occurrence of tonic extension, tonic flexion, clonic seizures and death. An active compound was capable of antagonizing the occurrence of the tonic extension which occurred immediately after the electroshock.

$ED_{50}$ values (and 95% confidence limits) are as follows:

| Compound | $ED_{50}$ mg/kg (95% confidence limits) |
|---|---|
| 1-(2-naphthoylmethyl)imidazole | 23 (20–25) |
| 1-[2-hydroxy-2-(2-naphthyl)-ethyl]imidazole | 74 (55–110) |
| 1-(1-naphthoylmethyl)imidazole | approx. 60 |
| 1-[2-hydroxy-2-(1-naphthyl)-ethyl]imidazole | 37 (32–53) |
| 1-[2,2-ethylenedioxy-2-(2-naphthyl)-ethyl]imidazole hydrochloride | 12 (9–14) |
| 1-[2,2-bis(ethylthio)-2-(2-naphthyl)-ethyl]imidazole hydrochloride | 35 (23–39) |
| 1-[2,2-ethylenedithio-2-(2-naphthyl)-ethyl]imidazole hydrochloride | 26 (16–38) |
| 1-[2,2-(2,2-dimethyl-1,3-propylenedioxy)-2-(2-naphthyl)ethyl]-imidazole hydrochloride | 26 (20–24) |
| 1-[2,2-(1,3-propylenedioxy)-2-(2-naphthyl)ethyl]imidazole hydrochloride | 17 (14–20) |
| 1-[2,2-bis(methylthio)-2-(2-naphthyl)-ethyl]imidazole hydrochloride | 32 (23–38) |
| 1-[2,2-ethylenedioxy-2-(1-naphthyl)-ethyl]imidazole hydrochloride | 19 (16–23) |
| 1-[2,2-(1-methyl-1,3-propylenedioxy)-2-(2-naphthyl)ethyl]imidazole hydrochloride | 19 (17–23) |
| 1-[2,2-(1,2-propylenedithio)-2-(2-naphthyl)ethyl]imidazole hydrochloride | 65 (55–73) |

EXAMPLE 17

Groups of 3 male ICR derived mice weighing 18–24 grams were given a single dose of compound intraperitoneally. The following doses were employed: 1, 3, 10, 30, 100, 300 or 1,000 mg/kg. After five days lethalities were determined. The $LD_{50}$ values are as follows:

| Compound | $LD_{50}$ (mg/kg) |
|---|---|
| 1-(2-naphthoylmethyl)imidazole | 100–300 |
| 1-[2,2-ethylenedioxy-2-(2-naphthyl)-ethyl]imidazole hydrochloride | 100–300 |
| 1-[2-hydroxy-2-(2-naphthyl)ethyl]-imidazole | 300–1000 |
| 1-[2-hydroxy-2-(1-naphthyl)ethyl]-imidazole | 300–1000 |
| 1-(1-naphthoylmethyl)imidazole | 100–300 |

EXAMPLE 18

The following illustrates a pharmaceutical composition for oral administration which may be prepared for the compounds of the present invention, e.g. 1-(2-naphthoylmethyl)imidazole or 1-[2,2-ethylenedioxy-2-(2-naphthyl)ethyl]imidazole hydrochloride,

|  | parts by weight |
| --- | --- |
| Active compound | 200 |
| Magnesium stearate | 3 |
| Starch | 30 |
| Lactose | 116 |
| Polyvinylpolypyrrolidone | 3 |

The above ingredients are combined and granulated using methanol as the solvent. The formulation is then dried and formed into tablets (containing 200 mg. of active compound each) with an appropriate tabletting machine.

What is claimed is:

1. A compound of the formula

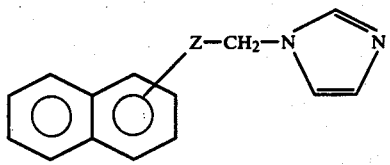

wherein Z is hydroxymethylene, hydroxymethylene esterified with an alkanoic acid having from one to eight carbon atoms or with benzoic acid, carbonyl, carbonyl protected as an acyclic ketal derived from a monohydric straight chain alkanol having from one to 4 carbon atoms, carbonyl protected as a cyclic ketal derived from a dihydric alcohol having two or three carbon atoms which may optionally be substituted by one or more methyl groups, carbonyl protected as an acyclic thioketal derived from a straight or branched alkylthiol having from one to four carbon atoms, carbonyl protected as a cyclic thioketal derived from an alkylene dithiol having two or three carbon atoms which may optionally be substituted by one or more methyl groups, or carbonyl protected as a cyclic hemithioketal derived from 2-mercaptoethanol or 3-mercapto-1-propanol; and the pharmaceutically acceptable acid addition salts thereof.

2. The compound of claim 1 wherein Z is carbonyl.

3. The compound of claim 2 which is 1-(2-naphthoylmethyl)imidazole and the pharmaceutically acceptable acid addition salts thereof.

4. The compound of claim 1 wherein Z is hydroxymethylene.

5. The compound of claim 4 which is 1-[2-hydroxy-2-(1-naphthyl)ethyl]imidazole and the pharmaceutically acceptable acid addition salts thereof.

6. The compound of claim 1 wherein Z is carbonyl-protected as an acyclic ketal derived from a monohydric straight chain alkanol having from one to four carbon atoms or carbonyl protected as a cyclic ketal derived from a dihydric alcohol having two or three carbon atoms which may optionally be substituted by one or more methyl groups.

7. The compound of claim 6 which is 1-[2,2-ethylenedioxy-2-(2-naphthyl)ethyl]imidazole and the pharmaceutically acceptable acid addition salts thereof.

8. The compound of claim 6 which is 1-[2,2-(1,3-propylenedioxy)-2-(2-naphthyl)ethyl]imidazole and the pharmaceutically acceptable acid addition salts thereof.

9. The compound of claim 6 which is 1-[2,2-ethylenedioxy-2-(1-naphthyl)ethyl]imidazole and the pharmaceutically acceptable acid addition salts thereof.

10. The compound of claim 1 wherein Z is carbonyl protected as an acyclic thioketal derived from a straight or branched chain alkylthiol having from one to four carbon atoms or carbonyl protected as a cyclic thioketal derived from an alkylene dithiol having two or three carbon atoms which may optionally be substituted by one or more methyl groups.

11. The compound of claim 10 which is 1-[2,2-bis(methylthio)-2-(2-naphthyl)ethyl]imidazole and the pharmaceutically acceptable acid addition salts thereof.

12. The compound of claim 10 which is 1-[2,2-bis(ethylthio)-2-(2-naphthyl)ethyl]imidazole and the pharmaceutically acceptable acid addition salts thereof.

13. A method for treating and preventing convulsions in a mammalian subject in need of such treatment comprising administering to said subject a therapeutically effective amount of a compound of the formula

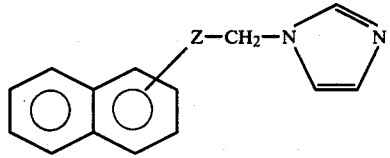

wherein Z is hydroxymethylene, hydroxymethylene esterified with an alkanoic acid having from one to eight carbon atoms or with benzoic acid, carbonyl, carbonyl protected as an acyclic ketal derived from a monohydric straight chain alkanol having from one to 4 carbon atoms, carbonyl protected as a cyclic ketal derived from a dihydric alcohol having two or three carbon atoms which may optionally be substituted by one or more methyl groups, carbonyl protected as an acyclic thioketal derived from a straight or branched alkylthiol having from one to four carbon atoms, carbonyl protected as a cyclic thioketal derived from an alkylene dithiol having two or three carbon atoms which may optionally be substituted by one or more methyl groups, or carbonyl protected as a cyclic hemithioketal derived from 2-mercaptoethanol or 3-mercapto-1-propanol, and the pharmaceutically acceptable acid addition salts thereof.

14. A pharmaceutical composition for the prevention and treatment of convulsions for the inhibition of gastric secretion in mammals comprising a therapeutically effective amount of a compound of the formula

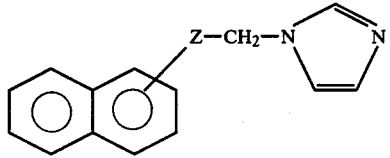

wherein Z is hydroxymethylene, hydroxymethylene esterified with an alkanoic acid having from one to eight carbon atoms or with benzoic acid, carbonyl, carbonyl protected as an acyclic ketal derived from a monohydric straight chain alkanol having from one to 4 carbon atoms, carbonyl protected as a cyclic ketal derived from a dihydric alcohol having two or three carbon atoms which may optionally be substituted by one or more methyl groups, carbonyl protected as an acyclic thioketal derived from a straight or branched alkylthiol having from one to four carbon atoms, carbonyl protected as a cyclic thioketal derived from an alkylene dithiol having two or three carbon atoms which may optionally be substituted by one or more methyl groups, or carbonyl protected as a cyclic hemithioketal derived from 2-mercaptoethanol or 3-mercapto-1-propanol, or a pharmaceutically acceptable acid addition salt thereof; in admixture with a pharmaceutically acceptable, non-toxic carrier.

15. A method for inhibiting gastric secretion in a mammalian subject in need of such treatment comprising administering to said subject a therapeutically effective amount of a compound of the formula

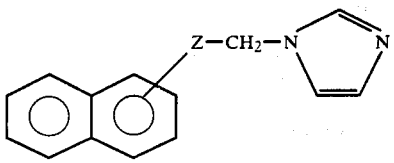

wherein Z is hydroxymethylene, hydroxymethylene esterified with an alkanoic acid having from one to eight carbon atoms or with benzoic acid, carbonyl, carbonyl protected as an acyclic ketal derived from a monohydric straight chain alkanol having from one to 4 carbon atoms, carbonyl protected as a cyclic ketal derived from a dihydric alcohol having two or three carbon atoms which may optionally be substituted by one or more methyl groups, carbonyl protected as an acyclic thioketal derived from a straight or branched alkylthiol having from one to four carbon atoms, carbonyl protected as a cyclic thioketal derived from an alkylene dithiol having two or three carbon atoms which may optionally be substituted by one or more methyl groups, or carbonyl protected as a cyclic hemithioketal derived from 2-mercaptoethanol or 3-mercapto-1-propanol, and the pharmaceutically acceptable acid addition salts thereof.

* * * * *